United States Patent [19]
Zinnen et al.

[11] Patent Number: 6,005,153
[45] Date of Patent: Dec. 21, 1999

[54] PROCESS FOR AROMATIC TRANSALKYLATION USING SIMULATED MOVING BED REACTIVE CHROMATOGRAPHY

[75] Inventors: Herman A. Zinnen, Evanston; Maureen L. Bricker, Buffalo Grove; Charles P. McGonegal, Addison, all of Ill.

[73] Assignee: UOP LLC, Des Plaines, Ill.

[21] Appl. No.: 09/175,116

[22] Filed: Oct. 19, 1998

[51] Int. Cl.$^6$ ....................................................... C07C 5/22
[52] U.S. Cl. ............................................. 585/475; 585/470
[58] Field of Search ...................................... 585/475, 470

[56] References Cited

U.S. PATENT DOCUMENTS

| | | | |
|---|---|---|---|
| 2,836,633 | 5/1958 | Esmay et al. | 260/671 |
| 3,122,494 | 2/1964 | Brown et al. | 208/63 |
| 3,211,798 | 10/1965 | Burk, Jr. et al. | 260/668 |
| 3,997,620 | 12/1976 | Neuzil | 260/674 SA |
| 3,998,901 | 12/1976 | Neuzil et al. | 260/674 SA |
| 4,028,428 | 6/1977 | Neuzil et al. | 260/674 SA |
| 4,079,094 | 3/1978 | Rosback et al. | 260/674 SA |
| 4,255,607 | 3/1981 | Miyake et al. | 585/805 |
| 5,530,172 | 6/1996 | Funk et al. | 585/736 |
| 5,530,173 | 6/1996 | Funk et al. | 585/736 |
| 5,744,683 | 4/1998 | Dandekar et al. | 585/736 |
| 5,744,684 | 4/1998 | Zinnen et al. | 585/737 |
| 5,877,373 | 3/1999 | Zinnen et al. | 585/475 |

FOREIGN PATENT DOCUMENTS

| | | | |
|---|---|---|---|
| 67656/90 | 11/1992 | Australia | C07C 15/42 |
| 2 031 096 | 3/1992 | Canada | 260/685 |

*Primary Examiner*—Walter D. Griffin
*Assistant Examiner*—Thuan D. Dang
*Attorney, Agent, or Firm*—Thomas K. McBride; Frank S. Molinaro; Maryann Maas

[57] ABSTRACT

A process for producing at least one $C_8$ alkylaromatic hydrocarbon product from a feedstock containing at least one $C_9$ or $C_{10}$ alkylaromatic hydrocarbon reactant using simulated moving bed reactive chromatography has been developed. At least a portion of the reactants are transalkylated to form at least one product in a zone of the simulated moving bed with concurrent separation of at least one alkylaromatic hydrocarbon using the adsorbent. The adsorbed alkylaromatic hydrocarbon is desorbed from the adsorbent in a subsequent zone of the simulated moving bed and the transalkylation of the reactants with concurrent separation of at least one alkylaromatic hydrocarbon using the adsorbent is continued.

22 Claims, 6 Drawing Sheets

PROCESS FOR AROMATIC TRANSALKYLATION USING SIMULATED MOVING BED REACTIVE CHROMATOGRAPHY

FIELD OF THE INVENTION

The invention is a process for aromatic transalkylation using simulated moving bed reactive chromatography.

BACKGROUND OF THE INVENTION $C_8$ alkylaromatic hydrocarbons are generally considered to be valuable products, and para-xylene in particular is in high demand. On the other hand, $C_9$ and $C_{10}$ alkylaromatic hydrocarbons are not nearly as valuable but are typically produced as a byproduct in the same aromatic production processes used to produce $C_8$ alkylaromatic hydrocarbons. Various approaches have been used to convert the less valuable $C_9$ and $C_{10}$ alkylaromatic hydrocarbons into $C_8$ alkylaromatic hydrocarbons. One popular approach has been to transalkylate $C_9$ and $C_{10}$ alkylaromatic hydrocarbons along with benzene or toluene to form the $C_8$ alkylaromatic hydrocarbons. Specifically, trimethylbenzenes and tetramethylbenzenes have been transalkylated along with benzene and toluene to form xylenes. However, transalkylation reactions are equilibrium limited and the product contains a mixture of unreacted $C_9$ and $C_{10}$ alkylaromatic hydrocarbons along with the desired $C_8$ alkylaromatic hydrocarbons. To increase conversion, commercial processes have utilized a two-stage design with the first stage being a fixed bed reactor and the second stage being a separation unit. Unreacted $C_9$ and $C_{10}$ alkylaromatic hydrocarbons present in the reactor product stream are separated and recycled to the reactor; see for example U.S. Pat. No. 3,211,798.

The present invention makes use of simulated moving bed reactive chromatography to perform the transalkylation. Reactive chromatography in general allows for concurrent reaction and separation of the unconsumed reactants from products, thereby extending product yields beyond thermodynamic equilibrium limitations. Reactive chromatography has been applied to other classes of chemical reactions; see for example U.S. Pat. No. 3,122,494 which describes an isomerization process having two sub-beds containing a mixture of catalyst and adsorbent where the feed is introduced between the two sub-beds and the desorbent introduction is alternated between the first sub-bed and the second sub-bed. The adsorbent must selectively adsorb straight-chain hydrocarbons to the substantial exclusion of non-straight-chain hydrocarbons. U.S. Pat. Nos. 5,530,172, 5,530,173, 5,744,684 and 5,744,683, incorporated by reference, all disclose using reactive chromatography in a simulated moving bed mode to effect alkane isomerization.

The present invention expands the application of simulated moving bed reactive chromatography to entirely new classes of chemical reactions, the transalkylation of alkylaromatic hydrocarbons. U.S. Pat. No. 2,836,633 describes alkylation of aromatic hydrocarbons using a catalyst supported on an adsorbent, but the purpose of using the adsorbent support was to increase the activity of the catalyst, not to perform a separation. CA2031096 and AU9067656-A describe an alkylation process where an alkene is adsorbed on a dry cationic exchange resin in its hydrogen form and is simultaneously reacted with an aromatic hydrocarbon. The present invention uses a simulated moving bed having a combination of catalyst and adsorbent in a single zone both to effect transalkylation and to concurrently separate the unconsumed $C_9$ and $C_{10}$ alkylaromatic hydrocarbons from the $C_8$ alkylaromatic hydrocarbon products, or to effect isomerization and separate the reactant from the isomerized product.

SUMMARY OF THE INVENTION

The purpose of the invention is to provide a process for producing at least one $C_8$ alkylaromatic hydrocarbon product from a feedstock containing at least a benzene or toluene reactant and at least one $C_9$ or $C_{10}$ alkylaromatic hydrocarbon reactant having at least one methyl or ethyl group. An embodiment of the invention is one where the simulated moving bed is present in a hydrogen atmosphere where the hydrogen to hydrocarbon mole ratio is in the range of about 0.1 to about 6 and is operated under conditions effective to transalkylate the reactants and form the $C_8$ alkylaromatic hydrocarbon product(s). The feedstock and a desorbent are continuously introduced into a simulated moving bed of a mixture of solids containing a catalyst effective to transalkylate the reactant and an adsorbent effective to selectively adsorb at least one alkylaromatic hydrocarbon. At least a portion of the reactants is transalkylated to form at least one product in a zone of the simulated moving bed with concurrent separation of at least one alkylaromatic hydrocarbon using the adsorbent. The adsorbed alkylaromatic hydrocarbon is desorbed from the adsorbent using the desorbent in a subsequent zone of the simulated moving bed and the transalkylation of the reactants with concurrent separation of at least one alkylaromatic hydrocarbon using the adsorbent is continued. The product(s) are removed and collected from the simulated moving bed.

DETAILED DESCRIPTION OF THE INVENTION

Figure 1:
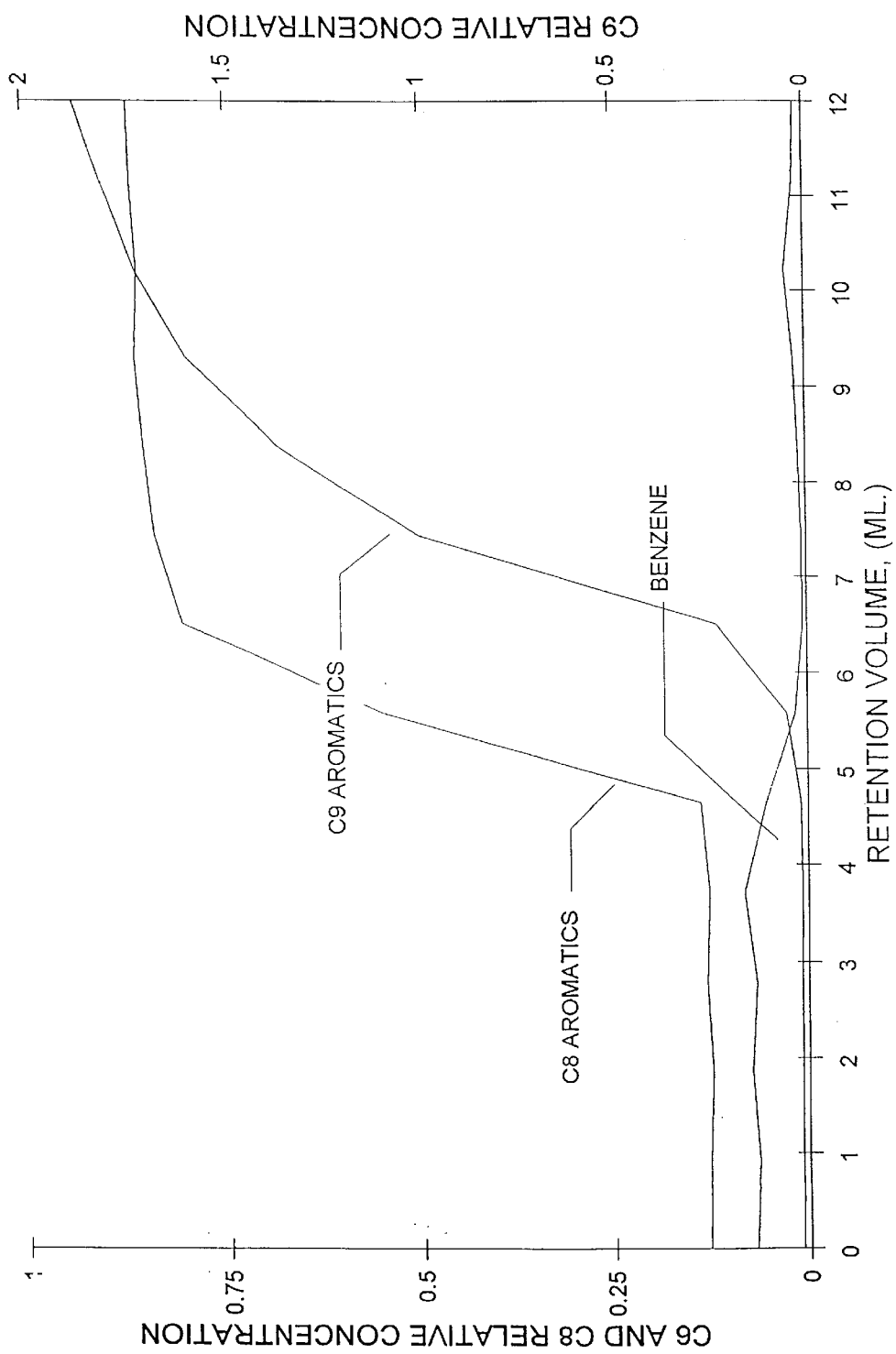
FIG. 1 is the chromatographic plot of the concurrent transalkylation of 1,2,4-trimethylbenzene and separation of the $C_8$ alkylaromatic hydrocarbon products using dealuminated Y zeolite as both the catalyst and adsorbent as described in Example 1. The $C_8$ alkylaromatic hydrocarbons are summed and the sum of the concentrations is plotted. Similarly, the $C_9$ alkylaromatic hydrocarbons are summed and the sum of the concentrations is plotted.

This invention is a process for overcoming the equilibrium limitations of a monocyclic $C_8$ alkylaromatic hydrocarbon production process using a simulated moving bed to effect reactive chromatography, i.e., a process where a simulated moving bed both catalyzes the reaction and effects the separation of at least one reactant from at least one product. The invention involves such molecular rearrangement as the transfer of the methyl groups of toluene to form benzene and xylenes or the transfer of the methyl groups of toluene, trimethylbenzenes, and tetramethylbenzenes to produce xylenes. Such reactions are referred to herein as transalkylation. In addition, the $C_9$ and $C_{10}$ alkylaromatic hydrocarbon reactants may undergo other types of reactions. For example, ethyl groups may be transalkylated or dealkylated, which is sometimes referred to as disproportionation, but is also referred to herein as transalkylation.

Both reactive chromatography and simulated moving bed technology are known in the art, and a general discussion of these technologies may be found in Mowry, J. R. In *Handbook of Petroleum Refining Processes;* Meyers, R. A. Ed.; McGraw-Hill: New York, 1986; pp 8–79 to 8–99 for the simulated moving bed technique; and *Preparative and Production Scale Chromatography;* Ganetsos, G., Barker, P. E., Eds.; Chromatographic Science Series Vol. 61; Marcel Dekker: New York, 1993; Chapters 16–21 for reactive chromatography. Applicants have discovered that these technologies may be effectively applied to the transalkylation of aromatics to form $C_8$ alkylaromatic hydrocarbon products, and the details of reactive chromatography and simulated moving bed technique as applied to the present invention are supplied below.

Reactive chromatography requires that the desired reaction and the separation of the products and reactants occur concurrently. Therefore, the simulated moving bed of the present invention must perform dual functions. The mixture of solids forming the simulated moving bed must be effective as a catalyst for the transalkylation reaction and also must be effective as an adsorbent for at least one of the reaction components. When the reactants enter the bed and contact the mixture of solids, the transalkylation reaction is catalyzed and products are formed. The reaction primarily takes place in the portion of the solid bed adjacent to and immediately downstream in the direction of the fluid flow of the introduction point of the feed, which contains at least one of the reactants. Not all the reactants will immediately react. Since the mixture of solids is also effective as an adsorbent for at least one reaction component, the components of the reaction begin to undergo separation. The reaction components which are less strongly adsorbed by the adsorbent are carried with the fluid flow, and the components which are strongly adsorbed by the adsorbent are carried countercurrently with the simulated movement of the solids. The migration of reaction components in opposite directions results in one region of the bed being richer in at least one component and one region of the bed being richer in at least one other component. Once separated, the reaction component carried by the fluid flow is removed from the simulated moving bed in a raffinate stream and collected. Concurrently, the reaction component carried by the adsorbent is desorbed by the introduction of a desorbent, removed from the simulated moving bed in an extract stream, and collected. If the desorbed reaction component is a reactant, after desorption it is still in contact with the simulated moving bed and may be catalytically reacted to form additional products. The process operates continuously with the reactants being introduced, the reaction being catalyzed, and at least one reaction component being separated from another reaction component and collected. Due to the continuous separation and removal of at least one of the reaction components, the thermodynamic equilibrium constraint of a static system is no longer a limiting factor and the transalkylation continues, resulting in a much greater conversion of reactants to products. As a result, the external recycle of unconsumed reactants is greatly reduced or eliminated, thereby affording a substantial savings in operating costs.

The catalyst and adsorbent mixture of solids, once chosen, is used in the process in the form of a simulated moving bed where the bed is held stationary, and the locations at which the various streams enter and leave the bed are periodically moved. The bed itself is usually a succession of fixed sub-beds, and different transalkylation reactions may require differing numbers of sub-beds. The most commonly used range is from about 4 sub-beds to about 24 sub-beds with the preferred range being from about 6 to about 24 sub-beds, and the most preferred range being from about 6 to about 12 sub-beds. The sub-beds are housed in individual interconnected chambers, and each chamber is equipped with an inlet and an outlet line.

The shift in the locations of input and output streams in the direction of the fluid flow through the bed simulates the movement of the solid bed in the opposite direction. Commercially, moving the locations of the input and output streams may be accomplished by a variety of fluid-directing devices such as rotary valves or a network of two-position or multi-position valves which work in conjunction with the inlet and outlet lines of the sub-beds. The fluid-directing device accomplishes moving the locations of the input and output streams through first directing the streams to the appropriate inlet or outlet lines of the sub-beds. After a specified time period called the step time, the fluid-directing device advances one index and redirects the streams to the inlet or outlet line immediately adjacent and downstream of the previously used inlet or outlet line. Each advancement of the fluid-directing device to a new position is generally called a step, and the completion of all the valve steps is called a cycle. The step time is uniform for each step in a cycle, and the cycle time ranges generally from about 5 minutes to about 3 hours. The principal inputs and outputs of the simulated moving bed system consist of four streams: the desorbent, the feed, the extract, and the raffinate. Each stream flows into or out of the simulated moving bed at individual locations and at a particular flow rate which is independently controlled.

In general terms, the reactants are contacted with a simulated moving bed of a mixture of solids effective to both catalyze the transalkylation and to separate at least one component of the transalkylation reaction. In the preferred embodiment, the $C_9$ and $C_{10}$ alkylaromatic hydrocarbon reactants are separated from the $C_8$ alkylaromatic hydrocarbon products through adsorption of at least the $C_9$ and $C_{10}$ alkylaromatic hydrocarbon reactants. The now separated $C_8$ alkylaromatic hydrocarbon products are continuously removed from the simulated moving bed and collected. The adsorbed $C_9$ and $C_{10}$ alkylaromatic hydrocarbon reactants are desorbed by a desorbent and, since they are still in contact with the simulated moving bed, they are catalytically isomerized to form additional $C_8$ alkylaromatic hydrocarbon products which are also separated and collected. The process continues in this fashion, with the $C_9$ and $C_{10}$ alkylaromatic hydrocarbon reactants being retained by the adsorbing properties of the simulated moving bed until they are transalkylated to form the desired $C_8$ alkylaromatic hydrocarbon products which are then separated and collected. This is a preferred embodiment because with the $C_9$ and $C_{10}$ alkylaromatic hydrocarbon reactants being adsorbed by the adsorbent, the desired $C_8$ alkylaromatic hydrocarbon products are carried with the fluid flow of the desorbent and have the least residence time in the simulated moving bed thereby reducing the opportunity for additional reaction of the desired products. Alternately, a less preferred embodiment is one where the adsorbent is chosen to have a greater selectivity for the desired $C_8$ alkylaromatic hydrocarbon products relative to that for the $C_9$ and $C_{10}$ alkylaromatic hydrocarbon reactants. The present invention will be described below mainly in terms of the preferred embodiment, with a summary of the distinct features of the less preferred embodiment.

It is a requirement that the simulated moving bed contain a catalyst effective for aromatic transalkylation. Such catalysts are well known in the art and suitable catalysts include, but are not limited to, catalytic composites containing at least mordenite, zeolite Beta, ZSM-5, dealuminated zeolite Y having a $SiO_2/Al_2O_3$ ratio in the range of from about 5 to about 25, and sulfated and/or tungstated zirconia. The dealuminated zeolite Y catalyst may be further ion exchanged with a Group IIA element, a Group IB element, or a Group VIII element or a mixture thereof. Some of these catalysts are described, and further references provided, in Meier, W. M.; Olson, D. H.; Baerlocher, Ch. Atlas of Zeolite Structure Types, $4^{th}$ Edition, Elsevier: Boston, 1996, pp. 152–153, 62–63, 146–147, and 104–105. Also, see generally, Kirk-Othmer *Encyclopedia of Chemical Technology*, $4^{th}$ ed.; Kroschwitz, J. I., Howe-Grant, M., Eds.; John Wiley & Sons: New York, vol. 4, pp. 83–84. A preferred catalyst is one containing mordenite. Depending upon the composition of the feed, several different catalysts may be combined in order to accomplish the catalysis function.

When choosing a catalyst, the operating temperature of the adsorbent that will be used must be considered. Both the adsorbent and the catalyst must be able to perform their respective functions at the same operating temperature. The simulated moving bed may be operated at $C_8$ alkylaromatic production operating conditions including temperatures ranging from 150° C. to 300° C. and pressures from atmospheric to 600 psig. The temperatures suggested here are lower than traditional operating temperatures since equilibrium favors $C_8$ alkylaromatic hydrocarbon formation at lower temperatures. The operating conditions should be chosen so that all components are in the same phase, gas or liquid. The gas phase allows higher mass transfer while the liquid phase provides higher adsorbent loading. Since many of the suitable adsorbents perform better at lower temperatures when using a physical mixture of adsorbent and catalyst, the preferred catalyst is mordenite due to its activity at lower temperatures. Ancillary added benefits of operating the process at a lower temperature include potentially extending the catalyst life and reducing the cost of the physical vessel(s) making up the simulated moving bed.

It is also required that the simulated moving bed contain an adsorbent capable of adsorbing at least one component of the transalkylation reaction. In the preferred embodiment, the adsorbent is selected to have either a pore size capable of retaining $C_9$ and $C_{10}$ alkylaromatic hydrocarbon reactants but not the $C_8$ alkylaromatic hydrocarbon products or to have a selectivity for $C_9$ and $C_{10}$ alkylaromatic hydrocarbon reactants. In other words, the adsorbent is capable of adsorbing $C_9$ and $C_{10}$ alkylaromatic hydrocarbons relative to $C_8$ alkylaromatic hydrocarbons at the simulated moving bed operating conditions. Any adsorbent meeting this criteria may be used in the process. Examples of suitable adsorbents include, but are not limited to, zeolite Beta, zeolite X, zeolite Y, and dealuminated zeolite Y having a $SiO_2/Al_2O_3$ ratio in the range of from about 5 to about 25. Zeolite Y may be ion exchanged with calcium, sodium, strontium, a Group IB element, a Group VIII element, or mixtures thereof and used successfully in the present invention. Similarly, dealuminated zeolite Y having a $SiO_2/Al_2O_3$ ratio in the range of from about 5 to about 25, and preferably from about 6 to about 12, may be ion exchanged with calcium, potassium, sodium, strontium, a Group IB element, a Group VIII element, or mixtures thereof and used successfully in the present invention. Structures of some of these adsorbents are described, and further references are provided, in Meier, W. M.; Olson, D. H.; Baerlocher, Ch. *Atlas of Zeolite Structure Types*, $4^{th}$ Edition, Elsevier: Boston, 1996, pp. 62–63 and 104–105. See also U.S. Pat. No. 4,940,830 which is incorporated by reference. A preferred adsorbent is zeolite Y ion exchanged with sodium, and a most preferred adsorbent is zeolite Y-54 ion exchanged with sodium and strontium; see Example 4. As with the catalyst, two or more adsorbents may be used within the simulated moving bed.

Particular adsorbents may retain the individual isomers of $C_8$ alkylaromatic hydrocarbons differently, which may be advantageous in specific applications. For example, zeolite Beta has greater selectivity for para-xylene and ortho-xylene as compared to meta-xylene; see Example 2. Therefore, a product stream may be withdrawn that is particularly enriched in meta-xylene as compared to para-xylene and ortho-xylene. Similarly, zeolite Y ion exchanged with sodium has a greater selectivity for meta-xylene as compared to para-xylene and ortho-xylene; see Example 3. Therefore, a product stream may be withdrawn that is depleted in meta-xylene as compared to an equilibrium mixture of all $C_8$ alkylaromatic hydrocarbon isomers.

The catalyst and adsorbent may be present in the simulated moving bed in a variety of ways with the catalyst to adsorbent volume ratio ranging from about 0.01 to about 1.0. It is preferred that the particles be present in a mixture and it is most preferred that the mixture be a homogeneous mixture of adsorbent and catalyst particles which is distributed throughout the simulated moving bed. Although less preferred, it is possible that the particles may be structured in alternating layers, sections, or cells as is known in the reactive chromatography art. For example, a vessel could contain a thin layer of catalyst followed by a thin layer of adsorbent with the pattern repeating throughout the vessel. The simulated moving bed itself may be all contained within a single vessel or may be composed of a series of two or more segregated sub-beds that are sequentially connected. It is important, however, that the catalyst and adsorbent be structured so that the simulated moving bed is capable of performing reactive chromatography where the products are rapidly separated from reactants. Therefore, it would be unacceptable to have, for example, the simulated moving bed consist of only two sub-beds, one containing only catalyst and the other containing only adsorbent, or only three sub-beds with a catalyst-only sub-bed between two adsorbent-only sub-beds. To perform reactive chromatography the catalyst and adsorbent must be of sufficient integration with one another so that the equilibrium limitations of a fixed bed system are overcome. Furthermore, if the catalyst and adsorbent were not sufficiently integrated the product $C_8$ alkylaromatic hydrocarbons may undergo reversion to reactants wherever the simulated moving bed contains predominantly catalyst. Such reversion is undesirable and is to be avoided.

Note that in the present invention zeolite Beta and dealuminated zeolite Y are able to function as both an adsorbent and as a catalyst; see Examples 1 and 2. Therefore, the invention could be successfully practiced by using only zeolite Beta or only dealuminated zeolite Y in the simulated moving bed. Zeolite Beta or dealuminated zeolite Y would both catalyze the transalkylation reaction and adsorb the $C_9$ and $C_{10}$ alkylaromatic hydrocarbons. In particular applications, using only one type of particle may be advantageous since the overall loading, operation, regeneration, and maintenance of the simulated moving bed may be simplified. Because of these advantages, in some applications it may be preferred to use a single type of particle that is able to function as both an adsorbent and as a catalyst.

For catalyst stability, hydrogen may be introduced into the simulated moving bed. The hydrogen may be introduced in a variety of ways, any of which would be appropriate provided sufficient hydrogen is present where needed to furnish the catalyst stabilizing function. The hydrogen to hydrocarbon mole ratio in the simulated moving bed should be within a range from about 0.1 to about 6. The hydrogen may be introduced with, or independently of, the feed or the desorbent, but the hydrogen must be introduced in a fashion that does not significantly disturb the chromatography of the separation.

The desorbent must be capable of desorbing the $C_9$ and $C_{10}$ alkylaromatic hydrocarbon reactants. Examples of acceptable reactive desorbents include benzene and toluene. Non-reactive desorbents which could be fractionated from the effluent and recycled for reuse are also contemplated. It is preferred that the desorbent be capable of entering into the transalkylation reaction since the result would be an increase in the amount of $C_8$ alkylaromatic hydrocarbon products formed. For example, benzene or toluene desorbent would enter into the transalkylation reaction with the $C_9$ and $C_{10}$ alkylaromatic hydrocarbons and would form additional $C_8$ alkylaromatic hydrocarbon products. Toluene has the additional benefit of being able to undergo transalkylation (sometimes referred to as toluene disproportionation) where two moles of toluene react to form one mole of benzene and one mole of xylene. Therefore, the preferred desorbents are benzene and toluene or a mixture thereof, with toluene being the most preferred desorbent. While a nonreactive desorbent may perform the desorbent function, the incidental increase in product amount achieved with benzene and toluene would be foregone.

The feed to the process contains a benzene or toluene reactant and at least one reactant being a $C_9$ or $C_{10}$ alkylaromatic hydrocarbon containing at least one methyl or ethyl group. References herein to "$C_9$ or $C_{10}$ alkylaromatic hydrocarbon" are to be understood as limited to those alkylaromatic hydrocarbons having at least one methyl or ethyl group. If the desorbent is benzene or toluene, the feed need only contain at least one $C_9$ or $C_{10}$ alkylaromatic hydrocarbon reactant. The preferred $C_9$ and $C_{10}$ alkylaromatic hydrocarbon reactants are trimethylbenzenes and tetramethylbenzenes. Examples of specific suitable alkylaromatic hydrocarbon reactants include, but are not limited to, toluene, 1,3,5-trimethylbenzene, 1,2,4-trimethylbenzene, 1,2,3-trimethylbenzene, and the tetramethylbenzene isomers. Other alkylaromatic hydrocarbons such as methylethyl benzenes and propylbenzenes may be present in the feed, but may not contribute to the formation of valuable xylene products. However, methylethyl benzenes present in the feed would contribute to the formation of ethylbenzene, which may be a desired product in certain applications. The feed should not contain components that would significantly alter the capacities or selectivities of the desorbent or that would deactivate the catalyst. The feed may also be an effluent from an aromatics complex such as a platforming product after unreacted alkanes and the desired $C_8$ alkylaromatic hydrocarbons have been removed. The product stream withdrawn from the simulated moving bed will contain desorbent and the desired $C_8$ alkylaromatic hydrocarbon products which are usually ortho- meta- and para-xylenes. The product stream would also contain any benzene and unreacted toluene. The product stream may be purified using techniques such as distillation or crystallization. If methylethyl benzenes were present in the feed, a further desired component of the product stream may be ethylbenzene.

Typically in a commercial system, the four principal streams are spaced strategically throughout the simulated moving bed system and divide the sub-beds into three zones, each of which performs a different function. Zone I contains the sub-beds located between the feed input and the raffinate output. The majority of the transalkylation reaction and the adsorption of the $C_9$ and $C_{10}$ alkylaromatic hydrocarbon reactants takes place in this zone. Zone II contains the sub-beds located between the extract output and the feed input. In this zone, there is some further reaction as the more selectively adsorbed $C_9$ and $C_{10}$ alkylaromatic hydrocarbon reactants are desorbed and come into contact with the catalyst. Zone III contains the sub-beds located between the desorbent input and the extract output. The main purpose of this zone is to completely desorb all $C_9$ and $C_{10}$ alkylaromatic hydrocarbon reactants and any impurities or reaction by-products from the adsorbent.

Alternately, the adsorbent may be chosen to selectively adsorb the $C_8$ alkylaromatic hydrocarbon products relative to the $C_9$ and $C_{10}$ alkylaromatic hydrocarbon reactants at the operating conditions of the simulated moving bed. In this embodiment, the desorbent is selected to have either a pore size capable of retaining the $C_8$ alkylaromatic hydrocarbon products but not the $C_9$ and $C_{10}$ alkylaromatic hydrocarbon reactants or to have an affinity for the $C_8$ alkylaromatic hydrocarbon products. Any adsorbents meeting this criteria would be suitable. Examples of suitable adsorbents include, but are not limited to, zeolite Y ion exchanged with potassium, barium, or a mixture thereof and zeolite X ion exchanged with potassium, barium, or a mixture thereof.

Operationally, the difference in this specific embodiment from that described above is that the $C_8$ alkylaromatic hydrocarbon products will be adsorbed by the adsorbent and carried with the simulated movement of the solids. The $C_8$ alkylaromatic hydrocarbon products will be desorbed using the desorbents discussed above and removed from the simulated moving bed in an extract stream. The $C_9$ and $C_{10}$ alkylaromatic hydrocarbon reactants will be carried with the fluid flow and removed from the simulated moving bed in a raffinate stream. The $C_9$ and $C_{10}$ alkylaromatic hydrocarbon reactants may be recycled to the simulated moving bed. This embodiment is less preferred due to the increased residence time of the $C_8$ alkylaromatic hydrocarbon products within the simulated moving bed and hence the increased opportunity for the $C_8$ alkylaromatic hydrocarbons to undergo transalkylation to reform the $C_9$ and $C_{10}$ alkylaromatic hydrocarbons. Other operational parameters such as the catalyst, operating conditions, hydrogen to hydrocarbon mole ratio, feed components, desorbents, and catalyst to adsorbent ratio are as discussed above.

A particular adsorbent, zeolite X ion exchanged with potassium, has a greater selectivity for ethylbenzene as compared to xylenes, which would allow for a product stream enriched in ethylbenzene as compared to an equilibrium mixture of all $C_8$ alkylaromatic isomers.

EXAMPLE 1

A 70 mL column was loaded with 34.9 grams of a single 20–40 mesh compound which is capable of functioning both as a catalyst and as an adsorbent, dealuminated zeolite Y having a $SiO_2/Al_2O_3$ ratio of 6. The column was placed in a heated enclosure at 250° C. and maintained at process pressure of 28 psig using back pressure regulators. Toluene desorbent and hydrogen were directed into the columns at measured rates. A 20 mL pulse of 1,2,4-trimethylbenzene feed was introduced and the desorbent flow was resumed. The effluent of the system was condensed and analyzed by gas chromatography to obtain the composition of the effluent. FIG. 1 shows the concentration profiles of the effluent beginning with the background level of toluene desorbent and $C_8$ alkylaromatic hydrocarbons, the background level of $C_8$ alkylaromatic hydrocarbons is due to toluene disproportionation. The concentrations of each individual species in a carbon number class were summed and the sum of the concentrations plotted. A region of effluent enriched in $C_8$ alkylaromatic hydrocarbons elutes prior to a region enriched in $C_9$ alkylaromatic hydrocarbons showing that both transalkylation and separation are occurring.

EXAMPLE 2

Figure 2:
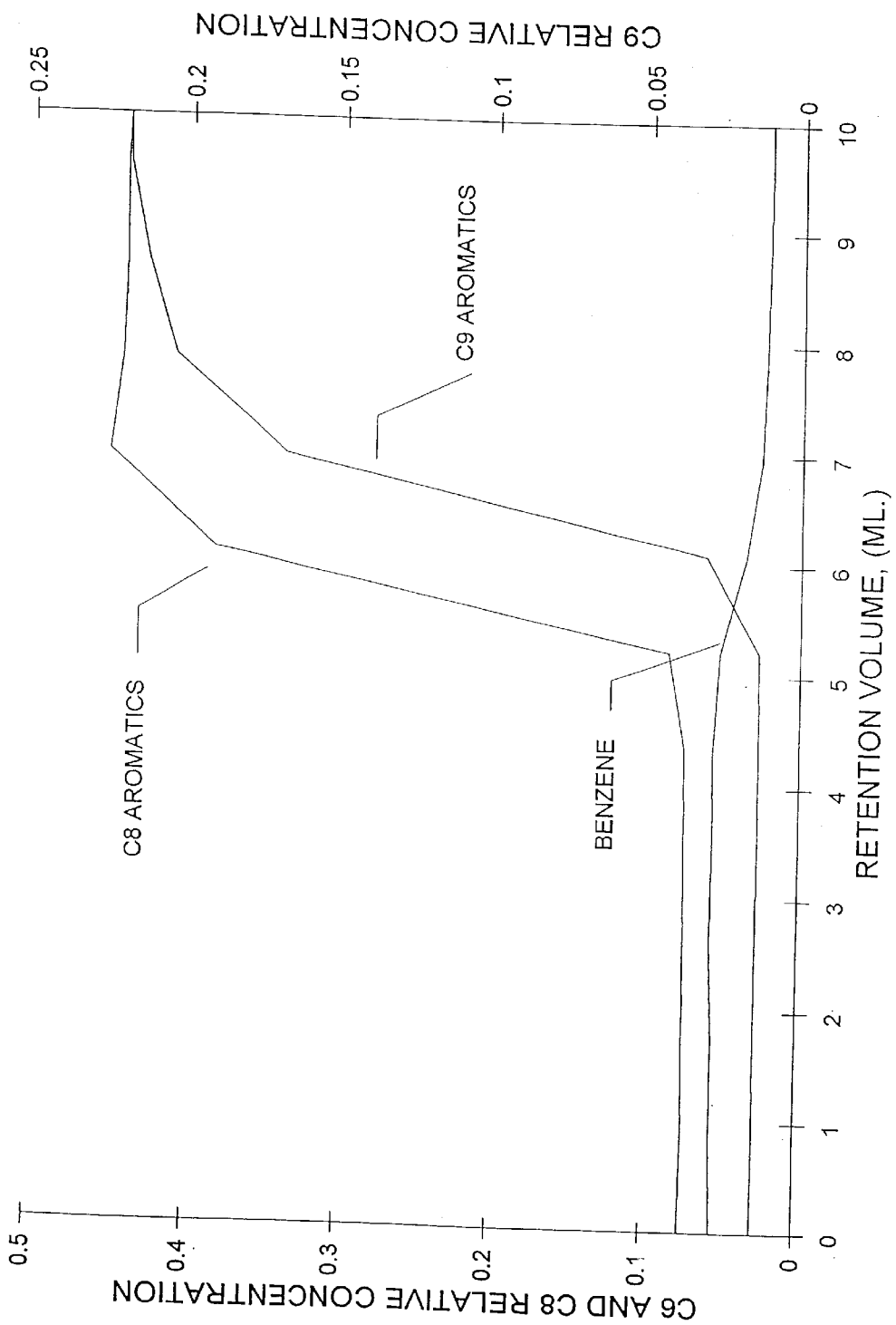
FIG. 2 is the chromatographic plot of the concurrent transalkylation of 1,3,5-trimethylbenzene and separation of the $C_8$ alkylaromatic hydrocarbon products using zeolite Beta as both the catalyst and adsorbent as described in Example 2. The $C_8$ alkylaromatic hydrocarbons are summed and the sum of the concentrations is plotted. Similarly, the $C_9$ alkylaromatic hydrocarbons are summed and the sum of the concentrations is plotted.
Figure 3:
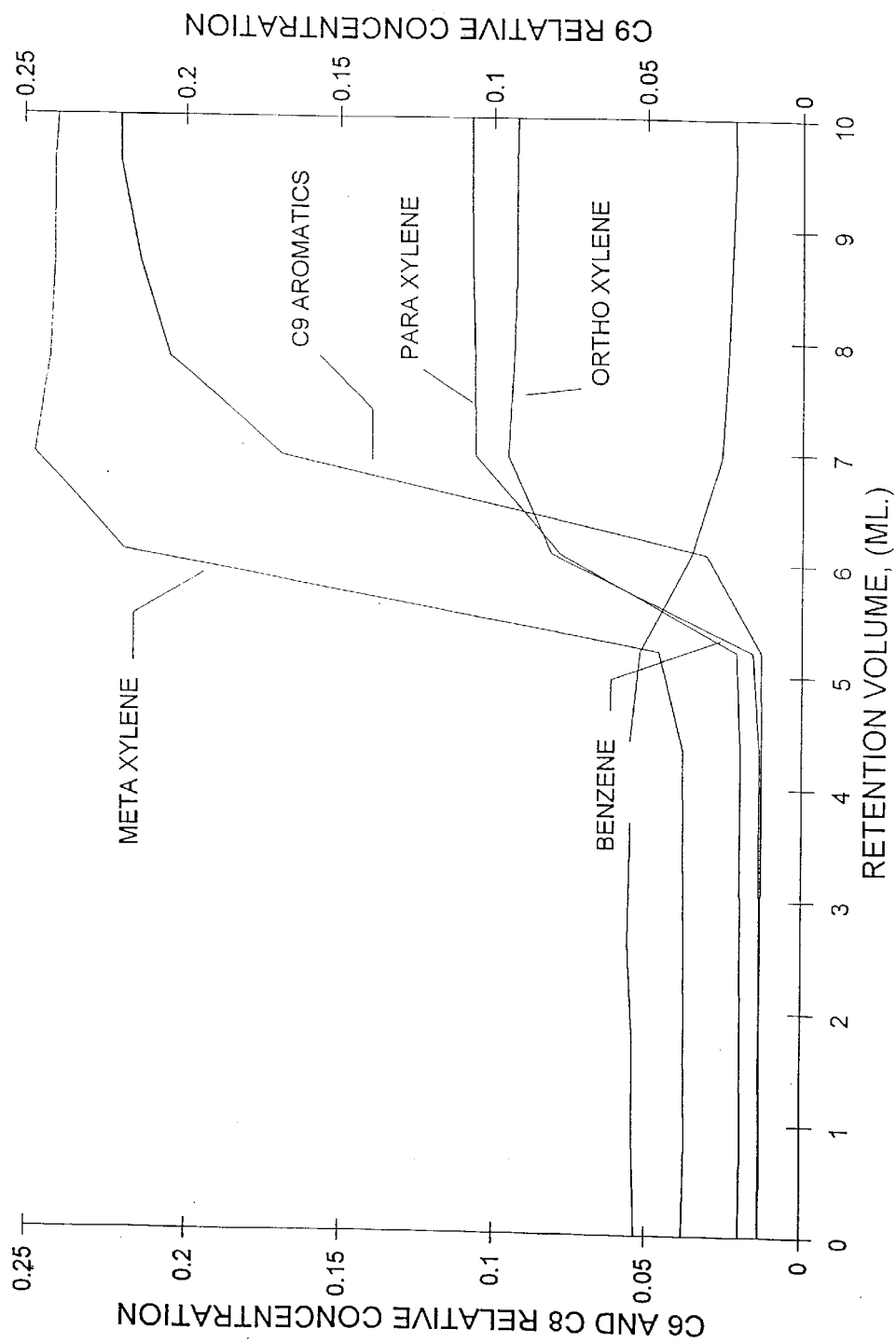
FIG. 3 is the chromatographic plot of the concurrent transalkylation of 1,3,5-trimethylbenzene and separation of the $C_8$ alkylaromatic hydrocarbon products using zeolite Beta as both the catalyst and adsorbent as described in Example 2. Each individual isomer of the $C_8$ alkylaromatic hydrocarbons is plotted and the $C_9$ alkylaromatic hydrocarbons are summed and the sum of the concentrations is plotted.

A 70 mL column was loaded with 32.1 grams of a single 20–40 mesh compound which is capable of functioning both as a catalyst and as an adsorbent, zeolite Beta. Zeolite Beta has the additional unique characteristic of selectively adsorbing para-xylene and ortho-xylene as compared to meta-xylene. The column was placed in a heated enclosure at 250° C. and maintained at process pressure of 28 psig using back pressure regulators. Toluene desorbent and hydrogen were directed into the columns at measured rates. A 20 mL pulse of 1,3,5-trimethylbenzene feed was introduced and the desorbent flow was resumed. The effluent of the system was condensed and analyzed by gas chromatography to obtain the composition of the effluent. FIG. 2 shows the concentration profiles of the effluent beginning with the background level of toluene desorbent and $C_8$ alkylaromatic hydrocarbons; the background level of $C_8$ alkylaromatic hydrocarbons is due to toluene disproportionation. In FIG. 2, the concentrations of each individual species in a carbon number class were summed and the sum of the concentrations plotted. A region of effluent enriched in $C_8$ alkylaromatic hydrocarbons elutes prior to a region enriched in $C_9$ alkylaromatic hydrocarbons showing that both transalkylation and separation are occurring. Furthermore, because of zeolite Beta's unique characteristic of selectively adsorbing para-xylene and ortho-xylene as compared to meta-xylene, the early eluting portion of the region of effluent enriched in $C_8$ alkylaromatic hydrocarbons is further enriched in meta-xylene. FIG. 3 shows the concentration of the individual $C_8$ alkylaromatic hydrocarbons species, para-xylene, meta-xylene and ortho-xylene, as well as the sum of the $C_9$ alkylaromatic hydrocarbons.

EXAMPLE 3

Figure 4:
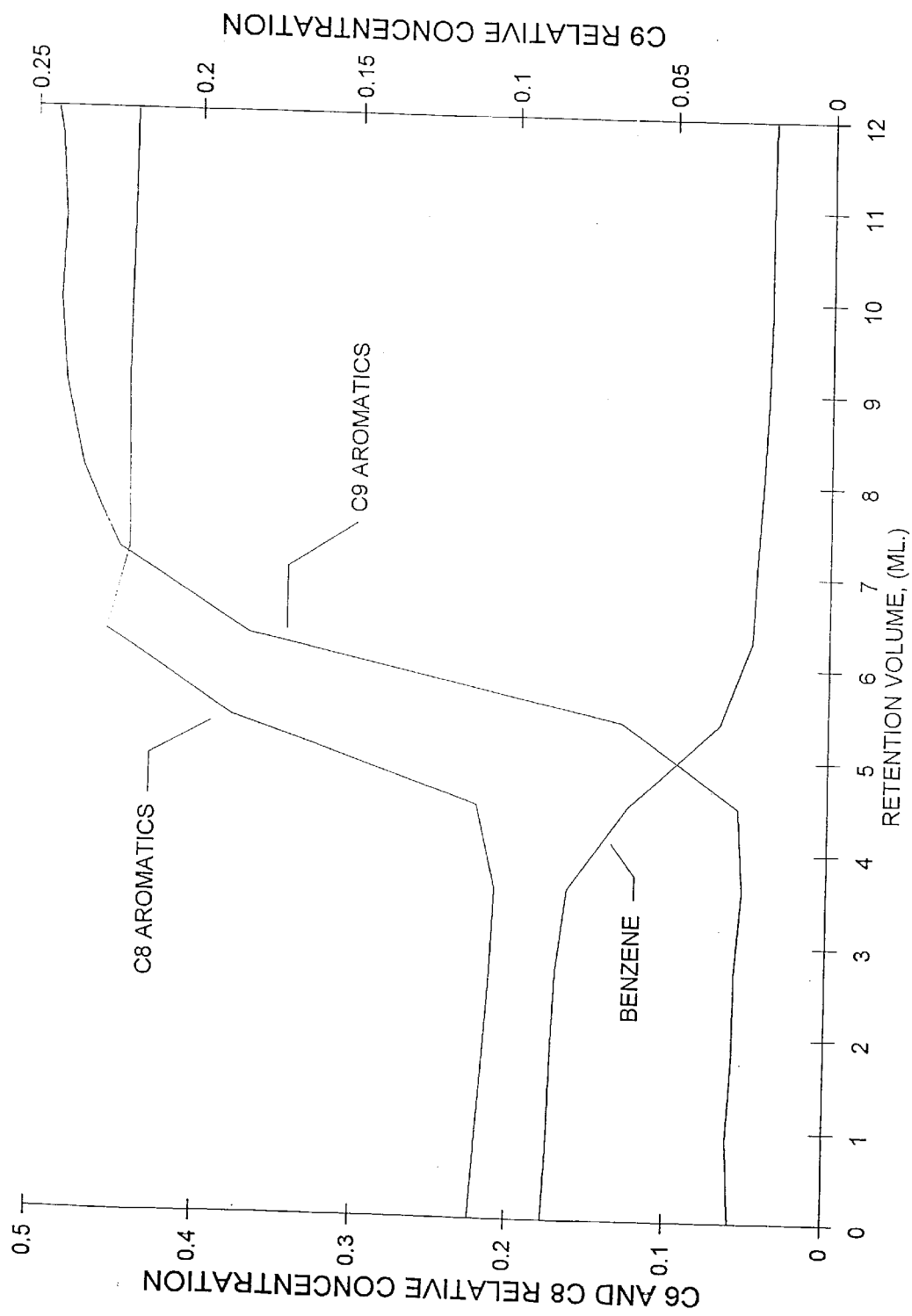
FIG. 4 is the chromatographic plot of the concurrent transalkylation of 1,3,5-trimethylbenzene and separation of the $C_8$ alkylaromatic hydrocarbon products using a homogeneous mixture of H-mordenite bound with alumina catalyst and Na-Y zeolite bound with clay adsorbent as described in Example 3. The $C_8$ alkylaromatic hydrocarbons are summed and the sum of the concentrations is plotted. Similarly, the $C_9$ alkylaromatic hydrocarbons are summed and the sum of the concentrations is plotted.

A 70 mL column was loaded with a homogeneous mixture of 20–40 mesh catalyst and adsorbent. The catalyst was H-mordenite bound with alumina (12.75 grams) and the adsorbent was Na-Y zeolite bound with clay (24.75 grams). The column was placed in a heated enclosure at 250° C. and maintained at process pressure of 62 psig using back pressure regulators. Toluene desorbent and hydrogen were directed into the columns at measured rates. A 20 mL pulse of a feed containing 50 mass percent toluene and 50 mass percent 1,3,5-trimethylbenzene was introduced and the desorbent flow was resumed. The effluent of the system was condensed and analyzed by gas chromatography to obtain the composition of the effluent. FIG. 4 shows the concentration profiles of the effluent beginning with the background level of toluene desorbent and $C_8$ alkylaromatic hydrocarbons; the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that both transalkylation and separation are occurring.

EXAMPLE 4

57 Grams of Na-Y-54 adsorbent containing 10.42 weight percent aluminum (volatile free) and 6.92 weight percent sodium (volatile free) were loaded into a column. 92 Grams of $SrCl_2.H_2O$ were dissolved in 3 liters of water and the resultant solution was circulated through the column for 20 hours at 70° C. and ambient pressure. The solution was drained from the column and the adsorbent rinsed with 5 L of water. The adsorbent was unloaded from the column and dried in a drying oven for about 16 hours in air at 90° C. The dried adsorbent was analyzed using an inductively coupled argon plasma atomic emission spectrophotometer to have 9.03 weight percent aluminum, 1.77 weight percent sodium, and 4.36 weight percent strontium, all on a volatile-free basis.

Figure 5:
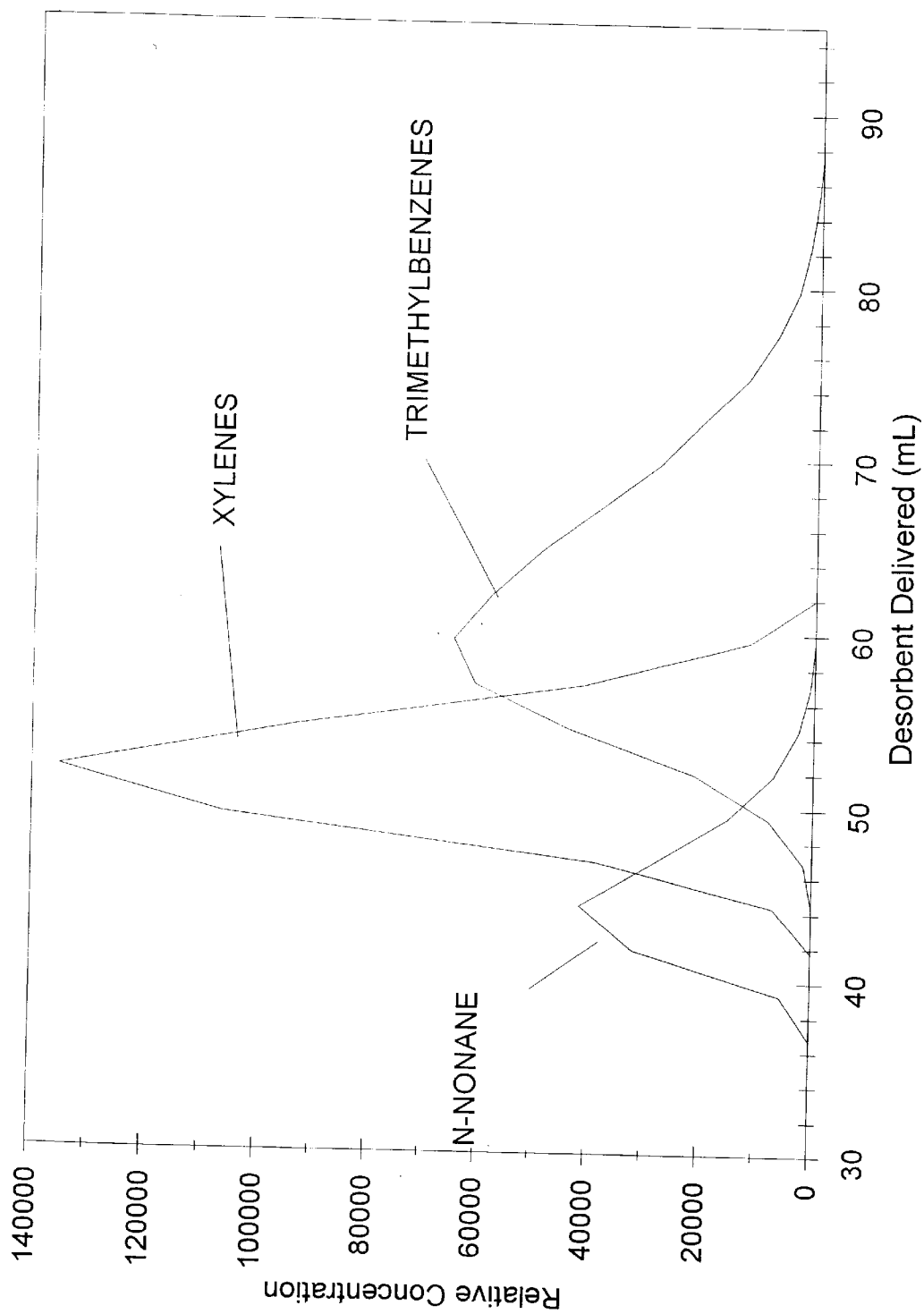
FIG. 5 is the chromatographic plot of the liquid phase separation of the $C_8$ alkylaromatic hydrocarbons from $C_9$ alkylaromatic hydrocarbons using a Na-Y zeolite ion exchanged with strontium adsorbent as described in Example 4. The $C_8$ alkylaromatic hydrocarbons are summed and the sum of the concentrations is plotted. Similarly, the $C_9$ alkylaromatic hydrocarbons are summed and the sum of the concentrations is plotted.

The column containing the dried adsorbent was placed in a heated enclosure at 150° C. and maintained at a pressure of 70 psig using back pressure regulators. Liquid phase toluene desorbent was directed into the columns at measured rates. A liquid phase 2 mL pulse of a feed containing equal parts normal nonane, ethylbenzene, para-xylene, meta-xylene, ortho-xylene, para-methylethylbenzene, meta-methylethylbenzene, ortho-methylethylbenzene, 1,2,3-trimethylbenzene, 1,2,4-trimethylbenzene and 1,3,5-trimethylbenzene was introduced and the desorbent flow was resumed. While in the column, the $C_8$ alkylaromatic hydrocarbons and $C_9$ alkylaromatic hydrocarbons were maintained in the liquid phase. The effluent of the system was analyzed by gas chromatography to obtain the composition of the effluent. FIG. 5 shows the concentration profiles of the effluent beginning with the background level of toluene desorbent. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation of the $C_8$ alkylaromatic hydrocarbons from the $C_9$ alkylaromatic hydrocarbons is occurring.

Figure 6:
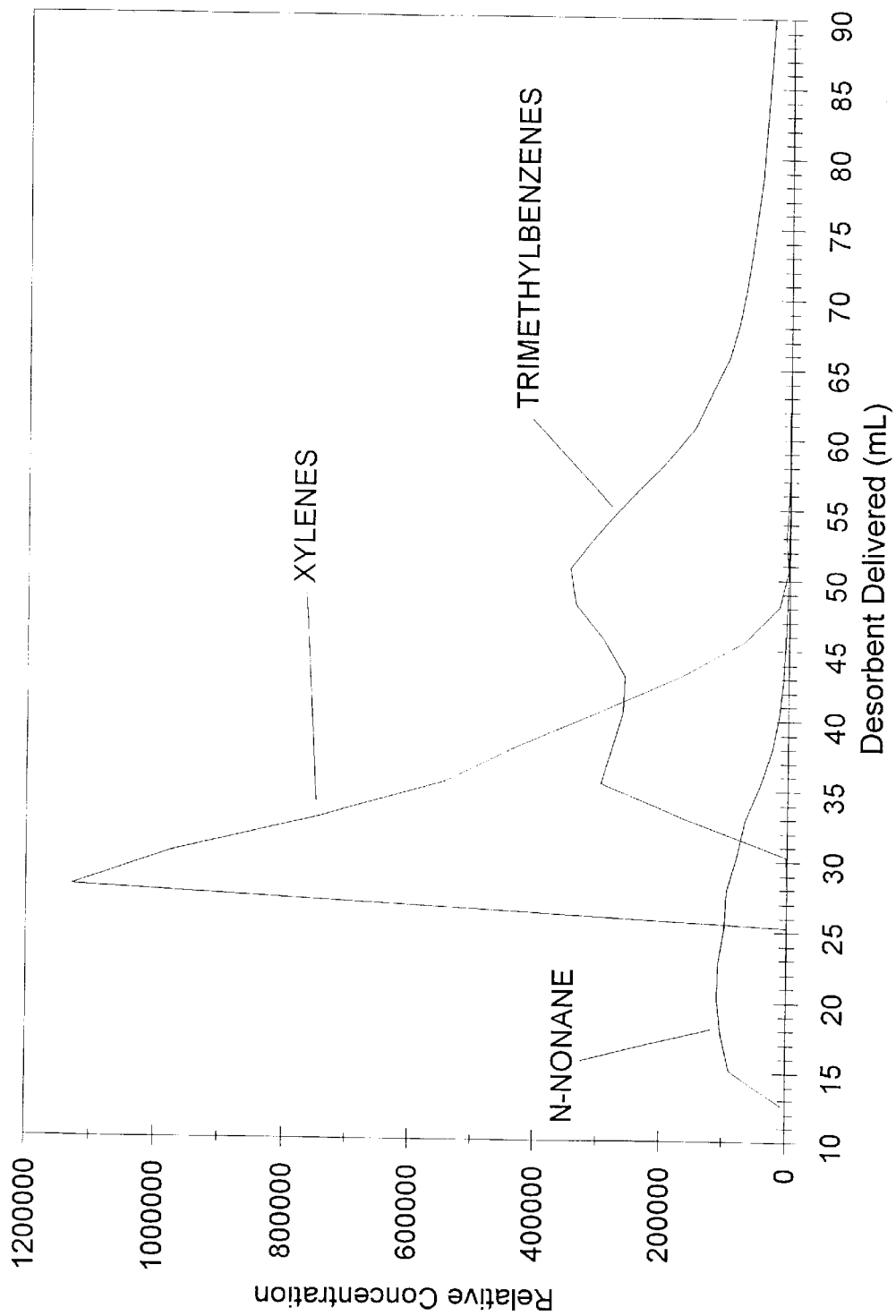
FIG. 6 is the chromatographic plot of the vapor phase separation of the $C_8$ alkylaromatic hydrocarbons from $C_9$ alkylaromatic hydrocarbons using a Na-Y zeolite ion exchanged with strontium adsorbent as described in Example 4. The $C_8$ alkylaromatic hydrocarbons are summed and the sum of the concentrations is plotted. Similarly, the $C_9$ alkylaromatic hydrocarbons are summed and the sum of the concentrations is plotted.

The pulse test was repeated with the components being maintained in the vapor phase. The column containing the dried adsorbent was again placed in a heated enclosure at 150° C. and maintained at a pressure of 10 psig using back pressure regulators. Toluene desorbent was directed into the columns at measured rates. A 20 mL pulse of a feed containing 32 mass percent toluene, 9.7 mass percent para-xylene, 14.8 mass percent meta-xylene, 9.4 mass percent ortho-xylene, 9.7 mass percent 1,3,5-trimethylbenzene, 20.0 mass percent 1,2,4-trimethyl benzene, and 4 mass percent 1,2,5-trimethylbenzene was introduced and the desorbent flow was resumed. While in the column, the $C_8$ alkylaromatic hydrocarbons and $C_9$ alkylaromatic hydrocarbons were maintained in the vapor phase. The effluent of the system was condensed and analyzed by gas chromatography to obtain the composition of the effluent. FIG. 6 shows the concentration profiles of the effluent beginning with the background level of toluene desorbent and $C_8$ alkylaromatic hydrocarbons; the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation of the $C_8$ alkylaromatic hydrocarbons from the $C_9$ alkylaromatic hydrocarbons is occurring.

What is claimed is:

1. A process for producing at least one $C_8$ alkylaromatic hydrocarbon product comprising:
   a) introducing a desorbent and a feedstock containing at least a benzene or toluene reactant and at least one $C_9$ or $C_{10}$ alkylaromatic hydrocarbon reactant having at least one methyl or ethyl group into a simulated moving bed comprising a mixture of a transalkylation catalyst and an adsorbent effective to selectively adsorb the $C_9$ or $C_{10}$ alkylaromatic hydrocarbon reactant(s) relative to the $C_8$ alkylaromatic hydrocarbon product(s) in the presence of hydrogen such that the hydrogen to hydrocarbon mole ratio is from about 0.1 to about 6;
   b) transalkylating, under transalkylation conditions, at least a portion of the reactants to form the $C_8$ alkylaromatic hydrocarbon product(s) in a zone of the simulated moving bed with concurrent separation of the $C_8$ alkylaromatic hydrocarbon product(s) from the $C_9$ or $C_{10}$ alkylaromatic hydrocarbon reactant(s) using the adsorbent;
   c) desorbing the $C_9$ or $C_{10}$ alkylaromatic hydrocarbon reactant(s) from the adsorbent using the desorbent in a subsequent zone of the simulated moving bed and continuing the transalkylation of the reactants with concurrent separation of the $C_8$ alkylaromatic hydrocarbon product(s) formed thereby from the $C_9$ or $C_{10}$ alkylaromatic hydrocarbon reactant(s) using the adsorbent; and
   d) removing and collecting the $C_8$ alkylaromatic hydrocarbon product(s) from the simulated moving bed.

2. The process of claim 1 wherein the catalyst is selected from the group consisting of mordenite, zeolite Beta, ZSM-5, dealuminated zeolite Y having a $SiO_2/Al_2O_3$ ratio in the range from about 5 to about 25, sulfated zirconia, tungstated zirconia, sulfated and tungstated zirconia and a combination thereof.

3. The process of claim 1 wherein the adsorbent is selected from the group consisting of zeolite Beta, zeolite X, zeolite Y, zeolite Y ion exchanged with a metal selected from the group consisting of calcium, sodium, strontium, a Group IB element, a Group VIII element, and mixtures thereof, dealuminated zeolite Y having a $SiO_2/Al_2O_3$ ratio in the range of from about 5 to about 25, dealuminated zeolite Y having a $SiO_2/Al_2O_3$ ratio in the range of from about 5 to about 25 and ion exchanged with a metal selected from the group consisting of calcium, potassium, sodium, strontium, a Group IB element, a Group VIII element and mixtures thereof, and a combination thereof.

4. The process of claim 1 wherein the adsorbent and catalyst are present in said simulated moving bed as a homogeneous mixture.

5. The process of claim 1 wherein the adsorbent and catalyst are identical.

6. The process of claim 1 wherein the desorbent is toluene, benzene, or a mixture thereof.

7. The process of claim 1 further characterized by purifying the product(s) removed from the simulated moving bed in step (d) using distillation or crystallization.

8. A process for producing at least one $C_8$ alkylaromatic hydrocarbon product comprising:
   a) introducing a feedstock containing at least one $C_9$ or $C_{10}$ alkylaromatic hydrocarbon reactant having at least one methyl or ethyl group and a desorbent containing at least toluene or benzene into a simulated moving bed comprising a transalkylation catalyst and an adsorbent effective to selectively adsorb the $C_9$ or $C_{10}$ alkylaromatic hydrocarbon reactant(s) relative to the $C_8$ alkylaromatic hydrocarbon product(s), in the presence of hydrogen such that the hydrogen to hydrocarbon mole ratio is in the range of about 0.1 to about 6;
   b) transalkylating, under transalkylation conditions, at least a portion of the $C_9$ or $C_{10}$ alkylaromatic hydrocarbon reactant(s) and at least a portion of the desorbent to form at least one $C_8$ alkylaromatic hydrocarbon product in a zone of the simulated moving bed with concurrent separation of the $C_8$ alkylaromatic hydrocarbon product(s) from the $C_9$ or $C_{10}$ alkylaromatic hydrocarbon reactant(s) using the adsorbent;
   c) desorbing the $C_9$ or $C_{10}$ alkylaromatic hydrocarbon reactant(s) from the adsorbent using the desorbent in a subsequent zone of the simulated moving bed and continuing the transalkylation of the $C_9$ or $C_{10}$ alkylaromatic hydrocarbon reactant(s) and desorbent with concurrent separation of the $C_8$ alkylaromatic hydrocarbon product(s) formed thereby from the $C_9$ or $C_{10}$ alkylaromatic hydrocarbon reactant(s) using the adsorbent; and
   d) removing and collecting the $C_8$ alkylaromatic hydrocarbon product(s) from the simulated moving bed.

9. The process of claim 8 wherein the catalyst is selected from the group consisting of mordenite, zeolite Beta, ZSM-5, dealuminated zeolite Y having a $SiO_2/Al_2O_3$ ratio in the range from about 5 to about 25, sulfated zirconia, tungstated zirconia, sulfated and tungstated zirconia, and a combination thereof.

10. The process of claim 8 wherein the adsorbent is selected from the group consisting of zeolite Beta, zeolite X, zeolite Y, zeolite Y ion exchanged with a metal selected from the group consisting of calcium, sodium, strontium, a Group IB element, a Group VIII element and mixtures thereof, dealuminated zeolite Y having a $SiO_2/Al_2O_3$ ratio in the range of from about 5 to about 25, dealuminated zeolite Y having a $SiO_2/Al_2O_3$ ratio in the range of from about 5 to about 25 and ion exchanged with a metal selected from the group consisting of calcium, potassium, sodium, strontium, a Group IB element, a Group VIII element, and mixtures thereof, and a combination thereof.

11. The process of claim 8 wherein the adsorbent and catalyst are present in said simulated moving bed as a homogeneous mixture.

12. The process of claim 8 wherein the adsorbent and catalyst are identical.

13. The process of claim 8 further characterized by purifying the $C_8$ alkylaromatic hydrocarbon product(s) removed from the simulated moving bed in (d) using distillation or crystallization.

14. A process for producing at least one $C_8$ alkylaromatic hydrocarbon product comprising:

a) introducing a desorbent and a feedstock containing at least a benzene or toluene reactant and at least one $C_9$ or $C_{10}$ alkylaromatic hydrocarbon reactant having at least one methyl or ethyl group into a simulated moving bed comprising a mixture of a transalkylation catalyst and an adsorbent effective to selectively adsorb the $C_8$ alkylaromatic hydrocarbon product(s) relative to the $C_9$ or $C_{10}$ alkylaromatic hydrocarbon reactant(s) in the presence of hydrogen such that the hydrogen to hydrocarbon mole ratio is in the range of about 0.1 to about 6;

b) transalkylating, under transalkylation conditions, at least a portion of the reactants to at least one $C_8$ alkylaromatic hydrocarbon product in a zone of the simulated moving bed with concurrent separation of the $C_8$ alkylaromatic hydrocarbon product(s) from the $C_9$ or $C_{10}$ alkylaromatic hydrocarbon reactant(s) using the adsorbent; and c) desorbing the $C_8$ alkylaromatic hydrocarbon product(s) from the adsorbent using the desorbent in a subsequent zone of the simulated moving bed and removing and collecting the $C_8$ alkylaromatic hydrocarbon product(s) from the simulated moving bed.

15. The process of claim 14 wherein the catalyst is selected from the group consisting of mordenite, zeolite Beta, ZSM-5, dealuminated zeolite Y having a $SiO_2/Al_2O_3$ ratio in the range of from about 5 to about 25, sulfated zirconia, tungstated zirconia, sulfated and tungstated zirconia, and a combination thereof.

16. The process of claim 14 wherein the adsorbent is selected from the group consisting of zeolite Y ion exchanged with potassium, barium, or a mixture thereof, zeolite X ion exchanged with potassium, barium, or a mixture thereof, and a combination thereof.

17. The process of claim 14 wherein the desorbent is toluene, benzene, or a mixture thereof.

18. The process of claim 14 further characterized by purifying the $C_8$ alkylaromatic hydrocarbon product(s) removed from the simulated moving bed in (c) using distillation or crystallization.

19. A process for producing at least one $C_8$ alkylaromatic hydrocarbon product comprising:

a) introducing a feedstock containing at least one $C_9$ or $C_{10}$ alkylaromatic hydrocarbon reactant having at least one methyl or ethyl group and a desorbent containing at least toluene or benzene into a simulated moving bed comprising a mixture of a transalkylation catalyst and an adsorbent effective to selectively adsorb the $C_8$ alkylaromatic hydrocarbon product(s) relative to the $C_9$ or $C_{10}$ alkylaromatic hydrocarbon reactant(s) in the presence of hydrogen such that the hydrogen to hydrocarbon mole ratio is in the range of about 0.1 to about 6;

b) transalkylating, under transalkylation conditions, at least a portion of the $C_9$ or $C_{10}$ alkylaromatic hydrocarbon reactant(s) and at least a portion of the desorbent to form at least one $C_8$ alkylaromatic hydrocarbon product in a zone of the simulated moving bed with concurrent separation of the $C_8$ alkylaromatic hydrocarbon product(s) from the $C_9$ or $C_{10}$ alkylaromatic hydrocarbon reactant(s) using the adsorbent; and c) desorbing the $C_8$ alkylaromatic hydrocarbon product(s) from the adsorbent using the desorbent in a subsequent zone of the simulated moving bed and removing and collecting the $C_8$ alkylaromatic hydrocarbon product(s) from the simulated moving bed.

20. The process of claim 19 wherein the catalyst is selected from the group consisting of mordenite, zeolite Beta, ZSM-5, dealuminated zeolite Y having a $SiO_2/Al_2O_3$ ratio in the range of from about 5 to about 25, sulfated zirconia, tungstated zirconia, sulfated and tungstated zirconia, and a combination thereof.

21. The process of claim 19 wherein the adsorbent is selected from the group consisting of zeolite Y ion exchanged with potassium, barium or a mixture thereof, zeolite X ion exchanged with potassium, barium, or a mixture thereof, and a combination thereof.

22. The process of claim 19 further characterized by purifying the product(s) removed from the simulated moving bed in (c) using distillation or crystallization.

* * * * *